United States Patent [19]

Florvall et al.

[11] Patent Number: 4,789,683
[45] Date of Patent: Dec. 6, 1988

[54] BENZAMIDO-DERIVATIVES

[75] Inventors: Gösta L. Florvall, Södertälje; Jan O. G. Lundström, Sollentuna; Sten I. Rämsby, Södertälje; Sven O. Ögren, Nykvarn, all of Sweden

[73] Assignee: Astra Lakemedel Aktiebolag, Sodertalje, Sweden

[21] Appl. No.: 689,502

[22] Filed: Jan. 8, 1985

Related U.S. Application Data

[63] Continuation of Ser. No. 350,816, Feb. 22, 1982, abandoned.

[30] Foreign Application Priority Data

Mar. 11, 1981 [SE] Sweden .............................. 8101536

[51] Int. Cl.$^4$ .................... A61K 31/40; C07D 207/09
[52] U.S. Cl. .................................... 514/428; 548/567
[58] Field of Search .................... 548/567; 424/274; 514/428

[56] References Cited

U.S. PATENT DOCUMENTS

| | | | |
|---|---|---|---|
| 3,342,826 | 9/1967 | Miller et al. | 424/274 X |
| 3,793,030 | 2/1974 | Asami | 96/91 R |
| 3,862,139 | 1/1975 | Podesva et al. | 260/326.47 |
| 3,914,418 | 10/1975 | Patchett et al. | 424/230 |
| 4,021,567 | 5/1977 | Kaplan et al. | 424/274 |
| 4,029,673 | 6/1977 | Bulteau | 548/567 |
| 4,172,143 | 10/1979 | Kaplan et al. | 548/567 X |
| 4,232,037 | 11/1980 | Florvall et al. | 424/274 |

FOREIGN PATENT DOCUMENTS

| | | |
|---|---|---|
| 695272 | 3/1967 | Belgium . |
| 0004831 | 10/1979 | European Pat. Off. . |
| 2459221 | 6/1975 | Fed. Rep. of Germany . |
| 2803651 | 3/1978 | Fed. Rep. of Germany . |
| 2901170 | 7/1979 | Fed. Rep. of Germany . |
| 2939914 | 4/1980 | Fed. Rep. of Germany . |
| 5916M | 1/1966 | France . |
| 60756 | 11/1965 | German Democratic Rep. . |
| 32712 | 7/1969 | Israel . |
| 19447 | 9/1978 | Japan . |
| 1234118 | 6/1971 | United Kingdom . |
| 1508880 | 4/1978 | United Kingdom . |

OTHER PUBLICATIONS

C.A., 90:38696c (1979), Ogata et al.
Chemical Abstracts, vol. 86:14800g "Thermal Development-Type Diazo Copying Materials" (1977).
Banker et al., *Modern Pharmaceutics* (Date not available), pp. 565–566; Marcel Dekkar, Inc., N.Y. and Basal.
*Pharmaceutics & Pharmacy Practice*, Banker et al. (Date not available), p. 118; J. B. Lippincott Co., Philadelpia and Toronto.

*Primary Examiner*—Joseph Paul Brust
*Attorney, Agent, or Firm*—Brumbaugh, Graves, Donohue & Raymond

[57] ABSTRACT

Novel therapeutically active compounds of the formula

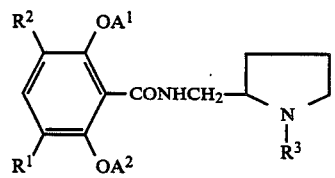

I wherein $R^1$ and $R^2$ are the same or different and each represents a hydrogen atom, a halogen atom, a cyano group, a lower alkyl group or an acyl group, $R^3$ is a lower alkyl group; an alkenyl group; or a benzyl group optionally substituted with fluorine, chlorine, bromine, trifluoromethyl, lower alkyl or lower alkoxy, $A^1$ and $A^2$ are the same or different and each represents a hydrogen atom, a lower alkyl group, an acyl group, an alkoxycarbonyl group or a dialkylcarbamyl group, provided that when $A^1$ and $A^2$ are the same lower alkyl group and $R^3$ is ethyl, $R^1$ or $R^2$ or both are selected among cyano, lower alkyl and acyl; or a physiologically acceptable salt or optical isomers thereof, methods for their preparation, pharmaceutical preparations containing the compounds and methods for their therapeutical use.

16 Claims, No Drawings

BENZAMIDO-DERIVATIVES

This application is a continuation of application Ser. No. 350,816, filed on Feb. 22, 1982, now abandoned.

DESCRIPTION

Field of the Invention

The present invention relates to novel, pharmacologically active derivatives of benzamide, intermediates and processes for their preparation, pharmaceutical compositions containing the benzamido-derivatives and to methods of their pharmacological use.

The object of the invention is to provide a benzamido-derivative useful in the treatment of emesis, psychosomatic disease and psychiatric disorders.

Prior Art

Sulphride, (U.S. Pat. No. 3,342,826) with the formula

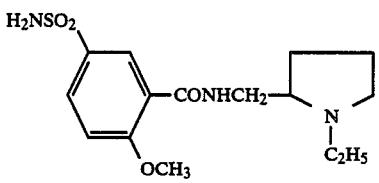

is a recently marketed antipsychotic agent. Sulpiride produces weak extrapy ramidal side effects in humans and weak catalepsy in experimental animals.

In U.S. Pat. No. 4,232,037 antipsychotic compounds of the formula

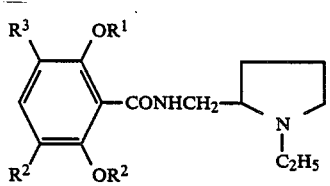

wherein $R^1$ is an alkyl group with 1–3 carbon atoms, $R^2$ and $R^3$ are the same or different and each is hydrogen, chlorine or bromine, are described. Among these compounds the compound of the formula

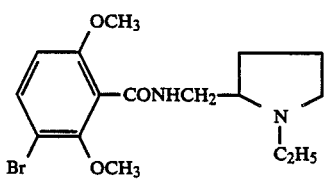

and with the designation FLA 731, is disclosed. The compounds of the U.S. Pat. No. 4,232,037 have a less potent antipsychotic effect than the compounds of the present invention.

DISCLOSURE OF THE INVENTION

The present invention relates to compounds of the formula

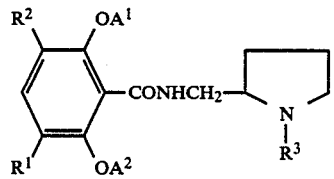

wherein $R^1$ and $R^2$ are the same or different and each represents a hydrogen atom, a halogen atom, a cyano group, a lower alkyl group or an acyl group, $R^3$ is a lower alkyl group; an alkenyl group; or a benzyl group optionally substituted with fluorine, chlorine, bromine, trifluoromethyl, lower alkyl or lower alkoxy, $A^1$ and $A^2$ are the same or different and each represents a hydrogen atom, a lower alkyl group, an acyl group, an alkoxycarbonyl group or a dialkylcarbamyl group, provided that when $A^1$ and $A^2$ are the same lower alkyl group and $R^3$ is ethyl, $R^1$ or $R^2$ or both are selected among cyano, lower alkyl and acyl; or a physiologically acceptable salt or optical isomers thereof.

It has been found that such compounds have valuable therapeutical properties.

The invention thus provides compounds, and physiologically acceptable salts thereof, which compounds are useful in therapeutic treatment of emesis, of psychosomatic diseases such as gastric and duodenal ulcer, and of psychiatric disorders such as depression, anxiety and especially psychoses e.g. schizofrenia.

Halogen atoms in formula I comprise chlorine, bromine, iodine and fluorine atoms.

Lower alkyl groups in formula I are straight or branched alkyl groups with 1 to 5 carbon atoms, such as methyl, ethyl, n-propyl, isopropyl, n-butyl, s-butyl, isobutyl, t-butyl, pentyl, 2-methylbutyl and 2,2-dimethylpropyl.

Acyl groups in formula I are groups alkyl—CO— wherein the alkyl moiety is defined as lower alkyl above.

Alkenyl groups in formula I are straight or branched hydrocarbon chains with 2–5 carbon atoms and one, two or more double bonds, e.g. vinyl, allyl, isopropenyl, but-2-enyl, buta-1,3-dienyl and pent-2-enyl.

Lower alkoxy groups in formula I are groups of alkyl—O— wherein the alkyl moiety is defined as lower alkyl above.

Alkoxycarbonyl groups in formula I are groups alkyl—O—CO— wherein the alkyl moiety is defined as lower alkyl above.

Dialkylcarbamyl groups in formula I are groups (alkyl)$_2$—N—CO— wherein the alkyl moiety is defined as lower alkyl above.

A first preferred sub-group of compounds of the invention is obtained whein in formula I $R^1$ and $R^2$ are the same or different and each represents a hydrogen atom, a halogen atom, a cyano group, a lower alkyl group or an acyl group, $R^3$ is a lower alkyl group; an alkenyl group or an optionally substituted benzyl group and one of $A^1$ and $A^2$ is a lower alkyl group and the other is a hydrogen atom.

Within this first sub-group compounds of the formula I wherein $R^1$ is bromine or chlorine and $R^2$ is hydrogen or bromine, $R^3$ is ethyl and one of $A^1$ and $A^2$ is methyl or ethyl and the other is hydrogen, are preferred.

A second preferred sub-group of compounds of the invention is obtained when in formula I $R^1$ and $R^2$ are the same or different and each represents a hydrogen atom, a halogen atom, a cyano group, a lower alkyl group or an acyl group, $R^3$ is a lower alkyl group; an alkenyl group or an optionally substituted benzyl group and one of $A^1$ and $A^2$ is a lower alkyl group and the other is an acyl group, an alkoxycarbonyl group or a dialkylcarbamyl group.

Within this second sub-group compounds of the formula I wherein $R^1$ is bromine, $R^2$ is hydrogen, $R^3$ is ethyl, $A^1$ is methyl and $A^2$ is acetyl, ethyloxycarbonyl or dimethylcarbamyl, are preferred.

A third preferred sub-group of compounds of the invention is obtained whein in formula I $R^1$ and $R^2$ are the same or different and each represents a hydrogen atom, a halogen atom, a cyano group, a lower alkyl group or an acyl group, $A^1$ and $A^2$ are the same or different and each represents a hydrogen atom, a lower alkyl group, an acyl group, an alkoxycarbonyl group or a dialkylcarbamyl group and $R^3$ is a lower alkyl group other than ethyl or an alkenyl group or an optionally substituted benzyl group.

Within this third sub-group compounds of the formula I wherein $R^1$ is chlorine or bromine, $R^{2-}$ is hydrogen, $A^1$ is methyl, $A^2$ is methyl and $R^3$ is methyl, n-propyl, allyl or benzyl, are preferred.

The new compounds of this invention may be used therapeutically as the racemic mixtures of (+)- and (−)-forms, which are obtained by synthesis. They may also be resolved into the corresponding enantiomers which, likewise, may be used in therapy. The (+)- and (−)-forms may also be obtained by the reaction of the corresponding enantiomeric 2-(aminomethyl)-1-alkyl-/alkenylpyrrolidone with the benzoic acid moeity.

The compounds of this invention may be administered in the form of free bases or their salts with non-toxic acids. Some typical examples of these salts are the hydrobromide, hydrochloride, phosphate, sulphate, sulphonate, citrate, lactate, maleate, and tartrate.

PHARMACEUTICAL PREPARATIONS

In clinical practice the compounds of the present invention will normally be administered orally, rectally or by injection in the form of pharmaceutical preparations comprising the active ingredient either as a free base or as a pharmaceutically acceptable non-toxic, acid addition salt, e.g. the hydrochloride, hydrobromide, lactate, acetate, sulphate, sulphamate and the like in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept.

The carrier may be a solid, semisolid or liquid diluent or capsule. These pharmaceutical preparations constitute a further aspect of this invention. Usually the active substance will constitute between 0.1 and 99% by weight of the preparation, more specifically between 0.5 and 20% by weight for preparation intended for injection and between 2 and 50% by weight for preparations suitable for oral administration.

To produce pharmaceutical preparations containing a compound of the invention in the form of dosage units for oral application, the selected compound may be mixed with a solid pulverulent carrier, e.g. lactose, saccharose, sorbitol, mannitol, starches such as potatostarch, corn starch or amylopectin, cellulose derivatives, or gelatine, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g. gum arabic, gelatine, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatine capsules (pearl-shaped closed capsules) consisting of gelatine and for example, glycerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatin rectal capsules comprising the active substance in admixture with vegetable oil or paraffin oil.

Liquid preparations for oral application may be in the form of syrups or suspensions for example, solutions containing from about 0.2% to about 20% by weight of the active substance herein described, the balance being sugar and a mixture of ethanol, water, glycerol, and propyleneglycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

Suitable peroral daily doses of the compounds of the invention are 100–500 mg, preferably 200–300 mg.

METHODS OF PREPARATION

The compounds of the invention may be obtained by one of the following methods.

A. The compounds of the formula

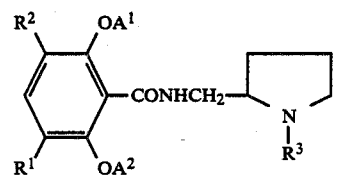

wherein $R^1$ and $R^2$ are the same or different and each represents a hydrogen atom, a halogen atom, a cyano group, a lower alkyl group or an acyl group, $R^3$ is a lower alkyl group; an alkenyl group; or a benzyl group optionally substituted with fluorine, chlorine, bromine trifluoromethyl, lower alkyl or lower alkoxy, $A^1$ and $A^2$ are the same or different and each represents a hydrogen atom, a lower alkyl group, an acyl group, an alkoxycarbonyl group or a dialkylcarbamyl group, provided that when $A^1$ and $A^2$ are the same lower alkyl group and $R^3$ is ethyl, $R^1$ or $R^2$ or both are selected among cyano, lower alkyl and acyl can be obtained by reaction of a compound of the formula

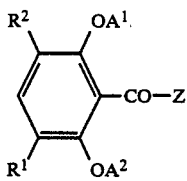   II wherein $R^1$, $R^2$, $A^1$ and $A^2$ have the definition given above and —CO—Z is a reactive group capable of reacting with an amino group under formation of an amide moiety with a compound of the formula

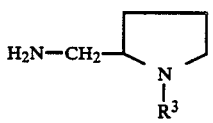   III wherein $R^3$ has the definition given above, or a reactive derivative thereof.

The reaction is carried out in a suitable solvent, such as diethyl ether, acetone, methylethyl ketone, chloroform or toluene between 0° C. and the boiling point of the reaction mixture. The resulting amine hydrochloride salt is readily recovered e.g. by filtration. Alternatively, the obtained salt is dissolved in water and converted to the free base using conventional techniques, such as the addition of sodium hydroxide solution.

Z in the acylating group —CO—Z may be a halogen group, such as chlorine or bromine, a hydroxy group or an organic residue.

The organic residue comprises groups which can form reactive acid derivatives. These can be carboxylic acid esters, e.g. methyl, ethyl, propyl, butyric, isobutyric and pentyl esters or comparable reactive esters, e.g. cyanomethyl or methoxymethyl ester, N-hydroxyimido ester or substituted or unsubstituted aromatic esters; acid hydrazides; acid azides; symmetrical anhydrides; mixed anhydrides for instance formed with lower alkylhalogenformates; azolides, e.g. triazolide, tetrazolide or imidazolide; or acid isocyanates.

According to the invention the following compounds can be used as reactive derivatives of the amine III: Reaction products of the amine with phosphorus chloride, phosphorus oxychloride, dialkyl, diaryl or o-phenylenechlorophosphites or alkyl or aryldichlorophosphites, or an isothiocyanate of the amine. The mentioned reactive derivatives can be reacted with the acid in situ or after previous isolation.

It is also possible to react the free acid and the free amine in the presence of a condensating agent, e.g. silicon tetrachloride, diphosphoruspentoxide or carbodiimides such as dicyclohexylcarbodiimide, N,N'-carbonyldiimidazole, N,N'-thionyldiimidazole, and diethyldiazodicarboxylate.

B. The compounds of the formula

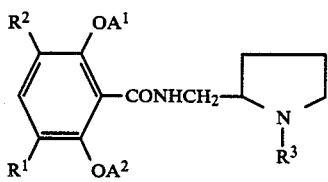

wherein $R^1$, $R^2$, $R^3$, $A^1$ and $A^2$ have the definition given above can be obtained by N-alkylation of a compound of the formula

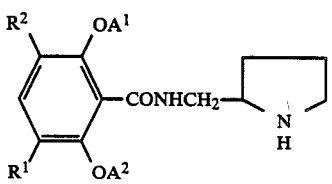

wherein $R^1$, $R^2$, $A^1$ and $A^2$ have the definition given above, with a compound of the formula

wherein $R^3$ has the definition give above and X is chlorine, bromine, sulphate, phosphate, benzenesulphonate or toluenesulphonate.

The reaction can be effected by treating the reactants at 50°–100° C. in a suitable solvent, e.g. acetone, alcohols, dimethylformamide (DMF), dimethylsulphoxide (DMSO) in the presence of a base, for example NaOH or $K_2CO_3$.

C. The compounds of the formula

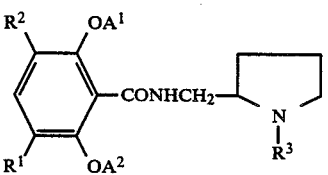

wherein $R^1$, $R^2$, $R^3$, $A^1$ and $A^2$ have the definition given above can be obtained by reaction of a compound of the formula

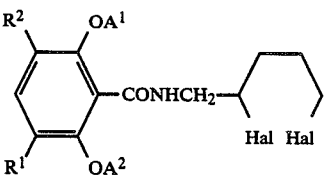

wherein $R^1$, $R^2$, $A^1$ and $A^2$ have the definition given above and Hal is Cl or Br with a compound of the formula

wherein $R^3$ has the definition given above.

The reaction is performed with the amine in excess, either without solvent or with a suitable solvent, such as lower alcohols, halogenated aliphatic hydrocarbons, DMF, DMSO at temperatures from 0° C. to 100° C.

D. The compounds of the formula

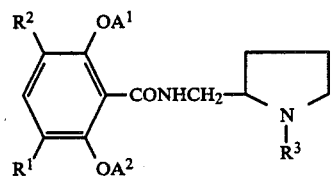

wherein $R^1$, $R^2$, $R^3$, $A^1$ and $A^2$ have the definition given above can be obtained by reduction of a compound of the formula

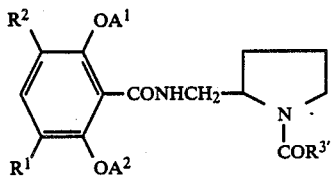

wherein $R^1$, $R^2$, $A^1$ and $A^2$ have the definition given above and $R^{3'}$ means the same as $R^3$ but for the content of carbon atoms, which is one less.

Suitable reducing agents working on the less sterically hindered amide group are (a) LiAlH$_4$ and alkoxy complexes thereof; (b) NaBH$_4$ with addition of transition metal salts, or AlCl$_3$ or BF$_3$ or POCl$_3$ or carboxylic acids such as CH$_3$COOH and CF$_3$COOH; c) B$_2$H$_6$.

The reaction is effected in alkyl ethers, such as diethylether, dimethoxyethane, diglyme, THF, dioxane, at temperatures from 0° C. to reflux temperatures of the reaction mixtures.

E. The compounds of the formula

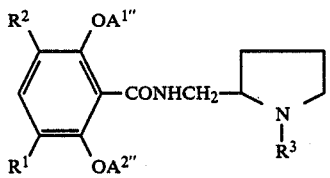

wherein $R^1$, $R^2$ and $R^3$ have the definition given above and $A^{1''}$ and/or $A^{2''}$ is a hydrogen atom and the other, when necessary, a lower alkyl group, can be obtained by dealkylation with a protonic acid or a Lewis acid of a compound of the formula

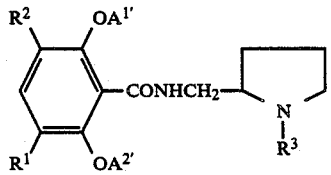

IV wherein $R^1$, $R^2$ and $R^3$ have the definition given above and $A^{1'}$ and $A^{2'}$ are lower alkyl groups.

Suitable protonic acids are e.g. HBr and HI.

Suitable Lewis acids are e.g. BBr$_3$, BCl$_3$, BF$_3$, AlCl$_3$ and AlBr$_3$.

Via selective dealkylation one of $A^{1'}$ and $A^{2'}$ ($A^{1'}$ and $A^{2'}$ are alkyl) in formula IV can be transferred to a hydrogen atom. By the selective dealkylation an equivalent amount of dealkylating agent is used.

Otherwise both $A^{1'}$ and $A^{2'}$ ($A^{1'}$ and $A^{2'}$ are alkyl) in formula IV can be transferred in the same reaction step to hydrogen atoms. By this procedure an excess of dealkylating agent is used.

The reaction is performed between 0°–20° C. in a halogenated lower aliphatic hydrocarbon, for example methylene chloride or chloroform. In the case of hydrogen halides acetic acid is preferred as solvent and the reaction is performed at elevated temperatures.

F. The compounds of the formula

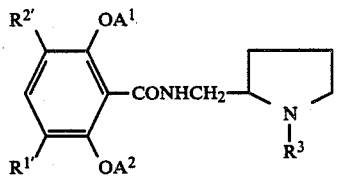

wherein $R^3$, $A^1$ and $A^2$ have the definition given above and $R^{1'}$ and/or $R^{2'}$ is a halogen atom, a lower alkyl group, an acyl group or a cyano group, and the other, when necessary, a hydrogen atom, can be obtained by halogenation with halogen or a halogen-dioxane complex, or reaction with an alkylhalide with Lewis acid catalysis or reaction with an acylhalide with Lewis acid catalysis or reaction with a cyanogen halide with Lewis acid catalysis, respectively, of a compound of the formula

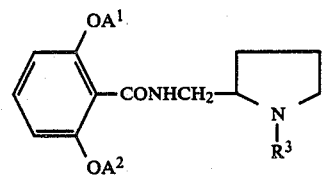

wherein $R^3$, $A^1$ and $A^2$ have the definition given above.

The introduction of a cyano group is accomplished by the action of trichloroacetonitrile or cyanogen halide in the presence of a Lewis acid.

Chlorination is effected by heating the starting compound with chlorine with or without Lewis acid catalysis or with HOCl, N-chloroamides in the presence of acid catalyst in suitable solvent e.g. chloroform, nitrobenzene.

Bromination is carried out with Br$_2$ with or without Lewis acid catalysis or bromination in acetic acid in the presence of a base e.g. sodium acetate or by using bromine-dioxane complex. Other reagents can be used among them HOBr and N-bromoamides especially N-bromosuccinimide with acid catalysis.

Acylations, alkylations and introduction of a cyano group are performed by using well-known Friedel-Crafts procedures.

G. The compounds of the formula

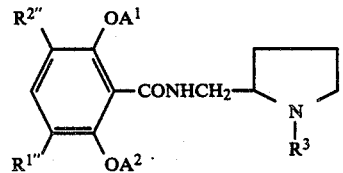

wherein $R^3$, $A^1$ and $A^2$ have the definition give above and $R^{1'''}$ and/or $R^{2'''}$ is halogen or cyano and the other, when necessary, a hydrogen atom, can be obtained by the reaction in a first step with NaNO$_2$ and in a second step with cuprous halogenide or cuprous cyanide of a compound of the formula

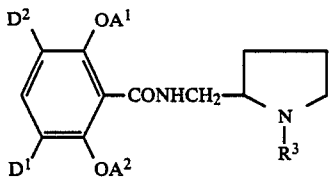

wherein $R^3$, $A^1$ and $A^2$ have the definition given above and $D^1$ and $D^2$ are the same or different and each represents a hydrogen atom or an amino group and at least one of $D^1$ and $D^2$ is an amino group.

Diazotation is performed in water at 0° C. with $NaNO_2$ in the presence of mineral acid. Compounds where $R^{1''}$ and $R^{2''}$ are Cl, Br or CN are performed by using a Sandmeyer reaction with CuBr, CuCl or CuCN. Compounds where $R^{1'''}$ and/or $R^{2''}$ is fluorine are prepared by heating the corresponding diazoniumtetrafluoborate salt in a dry state (Schiemann reaction).

The introduction of a cyano group is accomplished as described in Method F.

H. The compounds of the formula

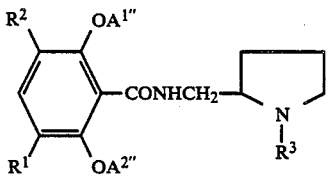

wherein $R^1$, $R^2$, $R^3$, $A^{1''}$ and $A^{2''}$ have the definition given above, can be obtained by reaction of a compound of the formula

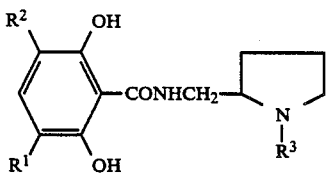

wherein $R^1$, $R^2$ and $R^3$ have the definition given above, with a compound of the formula

wherein $A^{1'}$ is a lower alkyl group and B is $-(SO_4)_{\frac{1}{2}}$, $-(PO_4)_{\frac{1}{3}}$ or halogen.

The reaction is effected selectively in a suitable solvent, e.g. acetone, DMF at elevated temperatures with one equivalent of alkylating agent in the presence of base, e.g. alkali metal carbonates or hydroxides.

I. The compounds of the formula

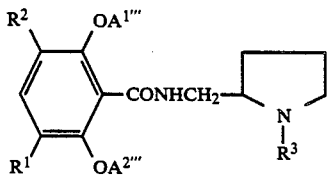

wherein $R^1$, $R^2$ and $R^3$ have the definition given above and $A^{1'''}$ and/or $A^{2'''}$ is an acyl group, an alkoxycarbonyl group or a dialkylcarbamyl group and the other, when necessary, a lower alkyl group, can be obtained by reaction of a compound of the formula

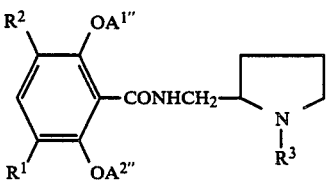

wherein $R^1$, $R^2$, $R^3$, $A^{1''}$ and $A^{2''}$ have the definition given above, with a compound of the formula

wherein R is an alkyl, alkoxy or dialkylamino group and Z' is Cl or Br.

The compounds wherein $A^{1'''}$ and/or $A^{2'''}$ are acyl are prepared by the reaction with the appropriate acid anhydride without solvent or in a suitable solvent such as benzene or chloroform with acid catalysis or by using a tertiary amine as solvent and/or catalyst.

The alkoxycarbonyl group and alkylcarbamyl group are introduced by the reaction of the corresponding halides in a suitable solvent in the presence of a tertiary amine.

INTERMEDIATES

The compounds of the formula

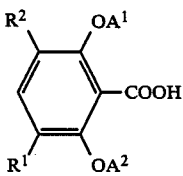

wherein $R^1$ and $R^2$ are the same or different and each represents a hydrogen atom, a halogen atom, a cyano group, a lower alkyl group or an acyl group and $A^1$ and $A^2$ are the same or different and each represents a hydrogen atom, a lower alkyl group, an acyl group, an alkoxycarbonyl group or a dialkylcarbamyl group, provided that when both $A^1$ and $A^2$ are a lower alkyl group, $R^1$ and $R^2$ are selected among cyano, lower alkyl and acyl and also provided that when $R^1/R^2$ is H, Cl or Br and $A^1/A^2$ is H or $CH_3$ the substituent of $R^1$ is different from the substituent of $R^2$ and the substituent of $A^1$ is different from the substituent of $A^2$, are valuable intermediates for the preparation of the compounds of this invention by the process A.

The intermediate benzoic acids can be prepared by reacting a compound of the formula

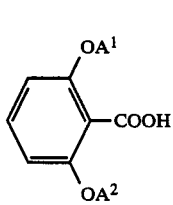

as follows:

(a) when $R^1$ and/or $R^2$ is Cl or Br: by chlorination or bromination for example as described under Method F above;
(b) when $R^1$ and/or $R^2$ is F: by fluorination for example as described under Method G above;
(c) when $R^1$ and/or $R^2$ is lower alkyl or acyl: by reacting with an alkylhalide or an acylhalide for example as described under Method F above;
(d) when $R^1$ and/or $R^2$ is cyano: by reacting with a cyanogen halide or trichloroacetonitrile with Lewis acid catalysis as described under Method F above.

Any of free acids can be converted to a compound of the formula II by esterification with for instance an acylhalogenide, an acylanhydride, a halogen formic acid ester or a dialkylcarbamyl halide.

Particularly preferred intermediates are those with the formulas

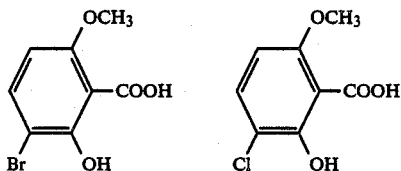

WORKING EXAMPLES

Example 1

N-Ethyl-2-(3-bromo-2,6-dihydroxybenzamidomethyl)-pyrrolidine

To 5.0 g (0.0118 mole) of N-ethyl-2-(3-bromo-2,6-dimethoxybenzamidomethyl)pyrrolidone in 125 ml of methylene chloride is added dropwise 7 ml (0.07 mole) of boron tribromide. The reaction mixture is left at room temperature for 9 days. It is then washed with 2M $NH_3$ and water, dried over $Na_2SO_4$ whereafter the solvent is evaporated. The residue is recrystallized from ethanol. Yield 0.3 g. M.p. 166°–8° C.

Example 2

N-Ethyl-2-(3-bromo-2-hydroxy-6-methoxybenzamidomethyl)pyrrolidone

To 5.0 g (0.0118 mole) of N-ethyl-2-(3-bromo-2,6-dimethoxybenzamidomethyl)pyrrolidine hydrochloride in 125 ml of methylene chloride is added 1.3 ml (0.0135 mole) of boron tribromide. A white precipitate is obtained. The reaction mixture is left for 2 hours at room temperature while stirring. It is then washed with 2M $NH_3$ and with water and the organic phase is dried over $Na_2SO_4$. Evaporation resulted in 4.1 g of product, which was recrystallized from ethanol. Yield 2.0 g (48%). M.p. 68.8°–69.4° C.

Example 3

(−)-N-Ethyl-2-(3-bromo-2-hydroxy-6-methoxybenzamidomethyl)pyrrolidine hydrochloride 10.0 g (0.025 ml) of (−)-N-ethyl-2-(3-bromo-2,6-dimethoxybenzamidomethyl)pyrrolidine is dissolved in 250 ml of methylene chloride. 2.6 ml (0.027 mol) of boron tribromide is added. The mixture is left over night at room temperature. It is then washed with 2N $NH_3$, dried over $Na_2SO_4$ and evaporated after addition of HCl-ether. The residue is dissolved in water and extracted with ether. The water phase is made alkaline with $NH_3$ and is extracted with chloroform. The chloroform phase is dried over $Na_2SO_4$ and evaporated. To the residue is added HCl-ether. The salt is filtered off, washed with ether and dried over $P_2O_5$. M.p.: sinterring at 100° C. Yield 6.6 g. Hygroscopic $[\alpha]_D^{20} = -45.5°$ (base).

Example 4

(−)-N-Ethyl-2-(3-chloro-2-hydroxy-6-methoxybenzamidomethyl)pyrrolidine hydrochloride 9.1 g (0.025 mole) of (−)-N-ethyl-2-(3-chloro-2,6-dimethoxybenzamidomethyl)pyrrolidine is dissolved in 250 ml of methylene chloride. 2.6 ml (0.027 mole) of boron tribromide is added. The mixture is left over night at room temperature. It is then washed with 2×100 ml of 2N $NH_3$ and 100 ml of water, dried over $Na_2SO_4$ and evaporated. The residue is dissolved in diluted HCl and extracted with ether. The water phase is made alkaline with $NH_3$ and is extracted with chloroform. The extract is dried over $Na_2SO_4$ and evaporated. The residue is dissolved in ether and HCl-ether is added. The precipitate is filtered off and dried over $P_2O_5$. M.p. sinterring at 100° C. Yield 7.4 g $[\alpha]_D^{20} = -51.4°$ (2% ethanol; pH 10.3).

Example 5

N-Ethyl-2-(3-bromo-6-ethoxy-2-hydroxybenzamidomethyl)pyrrolidine 5.0 g (0.0115 mole) of N-ethyl-2-(3-bromo-2,6-diethoxybenzamidomethyl)pyrrolidine hydrochloride is dissolved in 125 ml of methylene chloride. 1.25 ml (0.013 mole) of boron tribromide is added. The mixture is left for two hours at room temperature. It is then washed with 2M $NH_3$ and with water. The organic phase is dried over $Na_2SO_4$ and evaporated. The oily base obtained crystallizes after treatment with petroleum ether. The precipitate is filtered off and is recrystallized from ethanol. M.p. 83°–83.5° C. Yield 2.4 g (56%).

Example 6

(−)-N-Ethyl-2-(3-bromo-6-ethoxy-2-hydroxybenzamidomethyl)pyrrolidine 10.0 g (0.023 mole) of (−)-N-ethyl-2-(3-bromo-2,6-diethoxybenzamidomethyl)pyrrolidine is dissolved in 250 ml of methylene chloride. 2.4 ml (0.025 mole) of boron tribromide is added. The mixture is left over night at room temperature and is then washed with 2N $NH_3$. The extract is dried with $Na_2SO_4$ and evaporated. The oily residue crystallizes after a while. Petroleum ether is added to the product, which is then filtered off. Yield 7.0 g. M.p. 74°–76° C. $[\alpha]_D^{20} = -66.7°$ (1% acetone).

Example 7

(−)-N-Ethyl-2-(3,5-bromo-2-hydroxy-6-methoxybenzamidomethyl)pyrrolidine hydrochloride 44.0 g (10.1 mole) of (−)-2-(aminomethyl)-1-ethylpyrrolidine (−)ditartrate is dissolved in 200 ml of 20% NaOH. The mixture is then extracted with 2×100 ml of chloroform. The extract is dried with chloroform.

To 34.0 g (0.1 mole) of 3,5-dibromo-2,6-dimethoxybenzoic acid 40 ml of thionyl chloride and 300 ml of toluene are added. The mixture is heated while stirring an a steam bath for 30 minutes. Toluene and excess thionyl chloride are evaporated. To the residue is added the chloroform extract mentioned above. The mixture is heated for 10 minutes on a steam bath. The chloroform is then evaporated. The residue is dissolved in diluted HCl and the mixture is extracted with ether. The water phase is cooled and made alkaline with NaOH. The obtained precipitated is filtered off, dissolved in 500 ml of methanol, acidified with HCl-ether and evaporated. Yield 32.0 g (0.065 mole) of (−)-N-ethyl-2-(3,5-dibromo-2,6-dimethoxybenzamidomethyl)pyrrolidine hydrochloride. The product (0.065 mole) is dissolved in 500 ml of CHCl$_3$ and 6.3 ml (0.065 mole) of boron tribromide is added. The mixture is left over night at room temperature and is then washed with 2N NH$_3$ and water. The organic phase is dried with Na$_2$SO$_4$ and evaporated. The residue is dissolved in 400 ml of petroleum ether and the undissolved residue is filtered off. The ether is evaporated and the residue is dissolved in ether and acidified with HCl-ether. The precipitate is filtered off and dried over P$_2$O$_5$. Yield 27.3 g. M.p. sintering after a while. $[\alpha]_D^{20} = -8.6°$ (2% H$_2$O).

Example 8

N-Ethyl-2-(2-acetoxy-3-bromo-6-methoxybenzamidomethyl)pyrrolidine

To a suspension of 2-6-dimethoxybenzoic acid (80 g, 0.44 mole) in 1.5 l of dry chloroform was added dropwise with stirring a solution of 70.4 g bromine in 100 ml of dry chloroform during 3 h at 0° C. The solution is allowed to reach room temperature slowly during 20 h. The solvent was evaporated in vacuo and the residual crystalline mass was recrystallized from methanol giving 3-bromo-2-hydroxy-6-methoxybenzoic acid. Yield 82 g (76%). M.p. 143°–4° C.

3-Bromo-2-hydroxy-6-methoxybenzoic acid (24.6 g 0.1 mole) was dissolved in 50 ml of acetic anhydride. A few drops of conc. sulfuric acid was added and the mixture was heated at 60° C. during 20 h. After cooling about 100 mg of sodium bicarbonate was added and then icewater. The solvents were evaporated under reduced pressure. The residue was crystallized from diisopropylether to give 34.5 g (85%) of the desired acetoxy acid. M.p. 146°–7° C.

The preceeding acetoxy acid (5.8 g, 20 mmol) was dissolved in 30 ml of thionyl chloride. The solution was stirred at ambient temperature for 20 h. The solvent was evaporated and from the residue dry toluene was distilled twice. The resulting acid chloride (6 g) was used in the next step without further purification.

The crude acid chloride was dissolved in 50 ml of dry toluene and to this solution was added 1-ethyl-2-(aminomethyl)pyrrolidine (2,6 g, 20 mmol) in 10 ml of dry toluene at room temperature. Stirring was continued over night. The precipitate was filtered off and washed with dry toluene and dried. The crude amide hydrochloride was recrystallized from acetone to give the desired amine salt as white crystals. Yield 7.2 g (83%). M.p. 156° C. (dec.).

Example 9

N-Ethyl-2-(3-bromo-6-hydroxy-2-methoxybenzamidomethyl)pyrrolidine

To a solution of N-ethyl-2-(2,6-dimethoxybenzamidomethyl)pyrrolidine hydrochloride (23.0 g, 0.07 mole) in 300 ml of dry dichloromethane was added dropwise with stirring a solution of boron tribromide (17.5 g, 0.07 mole) in 25 ml of dry dichloromethane at 0° C. After the addition was completed the solution was allowed to reach room temperature over night. Water was added and pH adjusted to 7. The organic layer was washed with water and dried (MgSO$_4$). The solvent was evaporated in vacuo affording the title compound as a viscous oil (20 g) which was judged by TLC and GC analysis to be sufficiently pure for use in the next step without further purification.

A solution of bromine (4.3 g, 27 mmol) in 10 ml of glacial acetic acid was added dropwise with stirring to a solution of the preceeding crude amide (7.5 g, 27 mmol) in 100 ml of glacial acetic acid at room temperature. Stirring was continued for 15 h. The solvent was evaporated in vacuo to give a viscous oil (8.5 g). The product was analyzed by GC (3% OV-17) and consisted of 10% of the title 2-methoxy-3-bromo-6-hydroxy substituted isomer and 90% of the 2-hydroxy-3-bromo-6-methoxy substituted isomer. The desired phenol-isomer was isolated using preparative HPLC (SiO$_2$, CHCl$_2$+EtOH+conc. NH$_3$, 97+3+0.1). The solvent was evaporated in vacuo and the residual oil crystallized on standing. Yield 0.75 g. Recrystallization from n-hexane gave the pure title compound 0.6 g (6.5%). M.p. 62°–3° C.

Example 10

(−)-N-n-propyl-2-(3-bromo-2,6-dimethoxybenzamidomethyl)pyrrolidine

The title compound was prepared from 3-bromo-2,6-dimethoxybenzoic acid via the acylchloride and (−)-1-n-propyl-2-(aminomethyl)pyrrolidine in the same manner as described in Example 8. Yield 79%. M.p. 103°–104° C. $[\alpha]_D^{20} = -85.4°$ (c=0.5; CHCl$_3$).

Example 11

(−)-N-Ethyl-2-(3,5-dichloro-6-hydroxy-2-methoxybenzamidomethyl)pyrrolidine

The title compound was prepared from (−)-N-ethyl-2-(3,5-dichloro-2,6-dimethoxybenzamidomethyl)pyrrolidine by dealkylation in the same manner as described in Example 2. Yield 37%. M.p. 48°–49° C. (i-octane). $[\alpha]_D^{25} = -64°$ C. (c=1.26; CHCl$_3$).

Example 12

(−)-N-n-propyl-2-(3-bromo-2-hydroxy-6-methoxybenzamidomethyl)pyrrolidine hydrochloride The title compound was prepared from (−)-N-n-propyl-2-(3-bromo-2,6-dimethoxybenzamidomethyl)pyrrolidine by dealkylation in the same manner as described in Example 2. Yield 48%. M.p. (HCl) 140°–141° C. (acetone). $[\alpha]_D^{25} = -78°$ C. (c=0.80, EtOH) base.

Example 13

(−)-N-benzyl-2-(3-bromo-2-hydroxy-6-methoxybenzamidomethyl)pyrrolidine hydrochloride The title compound was prepared from (−)-N-benzyl-2-(3-bromo-2,6-dimethoxybenzamidomethyl)pyrrolidine by dealkylation in the same manner as described in Example 2. Yield 55%. M.p. (HCl) 207°–209° C. (EtOH).

Example 14

(−)-N-n-propyl-2-(3-bromo-6-hydroxy-2-methoxybenzamidomethyl)pyrrolidine hydrochloride The title compound was prepared from (−)-N-n-propyl-2-(3-bromo-2,6-dimethoxybenzamidomethyl)pyrrolidine by dealkylation in the same manner as described in Example 2. Yield 55%. M.p. (HCl) 137°–138° C. (acetone). $[\alpha]_D^{25} = -68°$ C. (c=0.12; MeOH).

In Table I are summarized physical data for the compounds prepared according to the description in the preceding examples were obtained. The NMR data were consistent with the assigned structures.

TABLE I

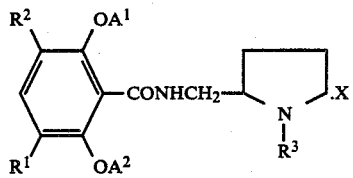

| Compound prepared in Example | R¹ | R² | R³ | A¹ | A² | X | M.P. °C. | $[\alpha]_D^{20°}$ | Analysis: Calculated % Found C | H | Br | Cl | N | O |
|---|---|---|---|---|---|---|---|---|---|---|---|---|---|---|
| 1 rac | Br | H | C₂H₅ | H | H | — | 166–68 | | 48.99 | 5.58 | | | 8.16 | 13.89 |
| | | | | | | | | | 48.0 | 5.53 | | | 7.68 | 14.1 |
| 2 rac | Br | H | C₂H₅ | CH₃ | H | — | 68–69 | | 50.43 | 5.92 | 22.37 | | 7.84 | 13.44 |
| | | | | | | | | | 50.4 | 5.99 | 22.4 | | 7.87 | 13.6 |
| 3 (−) | Br | H | C₂H₅ | CH₃ | H | HCl | sinters¹ | −45.5° (base) | 45.76 | 5.63 | | | 7.12 | 12.19 |
| 4 (−) | Cl | H | C₂H₅ | CH₃ | H | HCl | sinters¹ | −51.4° (base) | | | | 10.15 10.1 | 8.02 7.70 | |
| 5 rac | Br | H | C₂H₅ | C₂H₅ | H | — | 83–84 | | 51.76 | 6.24 | 21.52 | | 7.55 | 12.93 |
| | | | | | | | | | 51.7 | 6.09 | 21.4 | | 7.36 | 13.0 |
| 6 (−) | Br | H | C₂H₅ | C₂H₅ | H | — | 74–76 | −66.7° | 51.76 | 6.24 | 21.52 | | 7.55 | 12.93 |
| | | | | | | | | | 51.7 | 6.02 | 21.9 | | 7.31 | 13.1 |
| 7 (−) | Br | Br | C₂H₅ | CH₃ | H | HCl | sinters¹ | −8.6° | 38.12 | 4.48 | | | 5.93 | 10.16 |
| | | | | | | | | | 37.9 | 4.51 | | | 6.13 | 9.96 |
| 8 rac | Br | H | C₂H₅ | CH₃ | CH₃CO— | HCl | 156 (dec) | | 46.86 | 5.55 | 18.34 | 8.13 | 6.43 | |
| | | | | | | | | | 47.1 | 5.70 | 18.3 | 8.12 | 6.23 | |
| 9 rac | Br | H | C₂H₅ | H | CH₃ | — | 62–63 | | 51.73 | 6.08 | 20.36 | | 8.04 | |
| | | | | | | | | | 50.1 | 6.07 | 22.3 | | 7.44 | |
| 10 (−) | Br | H | CH₃(CH₂)₂— | CH₃ | CH₃ | — | 103–104 | −85.4° (base) | 52.99 | 6.54 | 20.74 | | 7.27 | |
| | | | | | | | | | 53.2 | 6.67 | 21.3 | | 7.18 | |
| 11 (−) | Cl | Cl | C₂H₅ | H | CH₃ | — | 48–49 | −64° | 51.88 | 5.80 | | 20.42 | 8.07 | 13.82 |
| | | | | | | | | | 51.74 | 5.70 | | 20.50 | 8.07 | 13.99 |
| 12 (−) | Br | H | CH₃(CH₂)₂— | CH₃ | H | HCl | 140–141 | −78° | 47.11 | 5.88 | 19.63 | 8.71 | 6.87 | |
| | | | | | | | | | 47.11 | 5.97 | 19.42 | 8.68 | 6.89 | |
| 13 (−) | Br | H | Ph—CH₂— | CH₃ | H | HCl | 207–209 | | | | | | | |
| 14 (−) | Br | H | CH₃(CH₂)₂— | H | CH₃ | HCl | 137–138 | −68° | 47.11 | 5.88 | 19.63 | 8.71 | 6.87 | |
| | | | | | | | | | 47.09 | 6.02 | 19.50 | 8.65 | 6.89 | |

¹Owing to hygroscopic properties the analytical values of this salt are unreliable. The absence of inpuritias was therefore examined by gas chromatography. The NMR of the compound was consistent with the proposed sturcture.

preceding examples.
NMR data for the compounds prepared according to

The compounds in the table below have been prepared by method A or by method E (the comounds wherein A¹=H)

TABLE I A

Structure: benzene ring with R² and OA¹ on one side, R¹ and OA² on other side, CONHCH₂-pyrrolidine (N-R³) substituent.

| Code | R¹ | R² | R³ | A¹ | A² | M.p. °C. | $[\alpha]_D^{20}$ | C | H | Br | Cl | N | O | F |
|---|---|---|---|---|---|---|---|---|---|---|---|---|---|---|
| FLA 925 | Br | H | Ph—CH₂— | CH₃ | CH₃ | | | | | | | | | |
| FLA 957(−) | C₂H₅ | H | C₂H₅ | CH₃ | CH₃ | 105-6 | −72° | | | | | | | |
| FLA 985 | CH₃(CH₂)₂ | H | C₂H₅ | CH₃ | CH₃ | 103-4 | | | | | | | | |
| FLB 130 | Cl | C₂H₅ | C₂H₅ | CH₃ | CH₃ | | | | | | | | | |
| FLA 964 | Br | C₂H₅ | C₂H₅ | CH₃ | CH₃ | 83-4 | | 69.04 | 9.12 | | | 7.92 | | |
| FLA 987 | C₂H₅ | C₂H₅ | C₂H₅ | CH₃ | CH₃ | | | 68.96 | 9.19 | | | 8.04 | | |
| FLB 189 | CH₃CO | H | C₂H₅ | CH₃ | CH₃ | | | | | | | | | |
| FLB | CH₃(CH₂)₂ | CH₃ | C₂H₅ | CH₃ | CH₃ | | | | | | | | | |
| FLB 168 | CH₃(CH₂)₂ | Cl | C₂H₅ | CH₃ | CH₃ | | | | | | | | | |
| FLA 981(−) | H | H | C₂H₅ | H | CH₃ | 141-2 | | 55.64 | 7.74 | | 10.95 | 8.65 | | |
| | | | | | | | | 55.92 | 7.24 | | 10.93 | 8.60 | | |
| | | | | | | | | 54.14 | 6.66 | | | 8.42 | | |
| FLA 954(−) | H | F | C₂H₅ | H | CH₃ | 154-5 | | | | | | | | 5.71 |
| FLA 961(−) | H | I | C₂H₅ | H | CH₃ | oil | | | | | | | | |
| FLA 965(−) | H | C₂H₅ | C₂H₅ | H | CH₃ | 101-2 | −72° | 59.55 | 7.94 | | 10.34 | 8.17 | | |
| FLA 986(−) | H | CH₃(CH₂) | C₂H₅ | H | CH₃ | 170-1 | −73° | 60.58 | 8.19 | | 9.93 | 7.85 | | |
| | | | | | | | | 60.56 | 8.21 | | 9.74 | 7.77 | | |
| FLA 968(−) | Br | Cl | C₂H₅ | H | CH₃ | 136-7 | | 43.74 | 5.10 | 19.44 | 8.62 | 6.80 | | |
| FLA 967(−) | Cl | Br | C₂H₅ | H | CH₃ | | | 43.82 | 5.20 | 19.53 | 8.63 | 6.78 | | |
| FLA 950(−) | F | Br | C₂H₅ | H | CH₃ | 145-6 | | 59.43 | 7.60 | | | 6.60 | | 4.61 |
| | | | | | | | | 59.27 | 7.55 | | | 6.53 | | 4.70 |
| FLA 988(−) | C₂H₅ | C₂H₅ | C₂H₅ | H | CH₃ | | | | | | | | | |
| FLA 966(−) | Br | C₂H₅ | C₂H₅ | H | CH₃ | 59-60 | | | | | | | | |
| FLA 974(−) | C₂H₅ | Br | C₂H₅ | H | CH₃ | | | | | | | | | |
| FLB 110(−) | H | H | C₂H₅ | H | CH₃ | 144-6 | | 54.12 | 6.94 | | 18.79 | 7.42 | | |
| FLB 131(−) | Cl | C₂H₅ | C₂H₅ | H | CH₃ | | | 54.20 | 7.04 | | 18.75 | 7.36 | | |
| | | | | | | | | 54.12 | 6.94 | | 18.79 | 7.42 | | |
| FLB 132(−) | C₂H₅ | Cl | C₂H₅ | H | CH₃ | 170-1 | | 54.35 | 6.94 | | 18.85 | 7.30 | | |
| | Br | H | C₂H₅ | CH₃ | C₂H₅OCO— | | | | | | | | | |

Example 15

The following examples illustrate the preparation of pharmaceutical compositions of the invention. The wording "active substance" denotes a compound according to the present invention or a salt thereof, and preferably the compound N-ethyl-2-(3-bromo-2-hydroxy-6-methoxy-benzamidomethyl)pyrrolidine or the 3-bromo-6-hydroxy-2-methoxy substituted isomer.

Formulation A

Soft gelatin capsules 500 g of active substance were mixed with 500 g of corn oil, whereupon the mixture was filled in soft gelatin capsules, each capsule containing 100 mg of the mixture (i.e. 50 mg of active substance).

Formulation B

Soft gelatin capsules 500 g of active substance were mixed with 750 g of pea nut oil, whereupon the mixture was filled in soft gelatin capsules, each capsule containing 125 mg of the mixture (i.e. 50 mg of active substance.

Formulation C

Tablets 50 kg of active substance were mixed with 20 kg of silicic acid of the trade mark Aerosil. 45 kg of potato starch and 50 kg of lactose were mixed therewith and the mixture was moistened with a starch paste prepared from 5 kg of potato starch and distilled water, whereupon the mixture was granulated through a sieve. The granulate was dried and sieved, whereupon 2 kg of magnesium stearate was mixed into it. Finally the mixture was pressed into tablets each weighing 172 mg.

Formulation D

Effervescing tablets 100 g of active substance, 140 g of finely divided citric acid, 100 g of finely divided sodium hydrogen carbonate, 3.5 g of magnesium stearate and flavouring agents (q.s) were mixed and the mixture was pressed into tablets each containing 100 mg of active substance.

Formulation E

Sustained release tablet 200 g of active substance were melted together with 50 g of stearic acid and 50 g of carnauba wax. The mixture thus obtained was cooled and ground to a particle size of at most 1 mm in diameter. The mixture thus obtained was mixed with 5 g of magnesium stearate and pressed into tablets each weighing 305 mg. Each tablet thus contains 200 mg of active substance.

Formulation F

Injection solution

| | |
|---|---|
| Active substance | 3.000 mg |
| Sodium pyrosulfite | 0.500 mg |
| Disodium edetate | 0.100 mg |
| Sodium chloride | 8.500 mg |
| Sterile water for inj. ad | 1.00 ml |

PHARMACOLOGY

Introduction

A number of studies suggest that the antipsychotic action of neuroleptic drugs is in some way related to the decrease in catecholamine transmission in the brain caused by these drugs and more specifically due to central dopamine (DA) receptor blockade in cortical and subcortical brain regions. Most compounds with an antipsychotic action affect several DA systems in the brain. There is evidence that the antipsychotic action may be linked to blockage of DA receptors in the subcortical and cortical limbic structures (J. Pharm. Pharmacol. 25, 346, 1973; Lancet, nov. 6. 1027, 1976) while the well-known extrapyramidal side effects produced by neuroleptic drugs are due to blockade of DA receptors in the nigroneostriatal DA system (Intern. J. Neurol. 6, 27–45, 1967).

There are presently several techniques available to study DA receptor blockage in the brain in vico. One method is based on the ability of antipsychotic drugs to block the behavioural effects induced by the DA agonist apomorphine in the rat. Several studies indicate an excellent correlation between the in vivo DA-receptor blockade as measured in the apomorphine test and therapeutic efficacy of different antipsychotic drugs. Apomorphine produces in rats and other species a characteristic syndrome consisting of repetitive movements (stereotypies) and hyperactivity which appear to be due to activation of postsynaptic DA receptors in the brain (J. Pharm. Pharmacol. 19, 627, 1967; J. Neurol. Transm. 40, 97–113, 1977). The stereotypies (chewing, likcing, biting) appear mainly to be induced via activation of DA receptors linked to the neostriatal DA system (J. Psychiat. Res., 11, 1, 1974) whereas the increased locomotion (hyperactivity) mainly appears to be due to activation of DA receptors in mesolimbic structures (nucleus olfactorium, nucleus accumbens) i.e. the mesolimbic DA-system. (J. Pharm. Pharmacol. 25, 1003, 1973)

A number of studies have demonstrated that neuroleptics of different structural classes block the apomorphine stereotypies in the rat and that this blockade is well related to blockade of DA transmission measured by biochemical or neurophysiological techniques. Thus, the antiapomorphine effect correlates well with changes in DA turnover produced by neuroleptic drugs (Eur. J. Pharmacol., 11, 303, 1970), DA receptor binding studies (Life Science, 17, 993–1002, 1976) and most importantly, with antipsychotic efficacy (Nature, 263, 388–341, 1976).

Methods

Male Sprague-Dawley rats (weighing 225–275 g) were used. The rats were observed in perspex cages (40 (L)×25 (w)×30 (h(cm) and the behaviour was scored 5, 20, 40, and 60 min. after apomorphine. The compounds were injected 60 min. prior to apomorphine hydrochloride (1 mg/kg) which was injected subcutaneously (s.c.) into the neck. This dose and form of administration was found to produce a very consistent response and very low variation in response strength. Furthermore, apomorphine given s.c. also produced a very consistent hyperactivity.

Directly after injection, the animals were placed in the cages, one in each cage. Scoring of the stereotypies were performed by two separate methods. The first scoring system was a modified version of the system introduced by Costall and Naylor (1973). The strength of the stereotype was scored on a 0–3 scale as follows:

| Score | Description of stereotyped behavior |
|---|---|
| 0 | No change in behavior compared to saline controls or sedated |
| 1 | Discontinous sniffing |
| 2 | Continous sniffing |
| 3 | Continous sniffing. Chewing, biting and licking. |

In the second system the number of animals displaying hyperactivity caused by apomorphine were scored. Each group consisted of 6–8 animals. Saline controls were always run simultaneously. $ED_{50}$'s are in the first scoring system (0–3 scale), the doses which reduce the strength of the stereotypies by 50% over the observation period of 60 min. $ED_{50}$'s of the second scoring system are the doses which reduce the number of animals showing hyperactivity by 50% over the observation period of 60 min. The $ED_{50}$ were calculated from log dose-response curves by the method of least squares from 4–6 dose levels with 6–8 animals per dose level.

Results

The results are presented in Table II. The compounds of the invention were compared with the prior art antipsychotic compounds sulpiride (Life Science, 17, 1551–1556, 1975) and N-ethyl-2-(3-bromo-2,6-dimethoxybenzamidomethyl)pyrrolidine (racemic and levorotatory) designated FLA 731 and FLA 731 (−), resp. The tabulated results indicate that the compounds of the present invention are potent inhibitors of DA receptors in the brain. Due to their ability to antagonize both apomorphine stereotypies and hyperactivity they probably block DA receptors in both striatal and limbic areas (see Introduction). The compounds of the invention are clearly more potent than prior art compounds FLA 731 and FLA 731 (−) (racemic and levo-rotary compounds compared separately) to inhibit apomorphine. Furthermore, they are considerably more potent than the antipsychotic drug sulpiride. Since there is a highly significant correlation between the blockade of apomorphine and clinical antipsychotic efficacy (Nature, 263, 338–341, 1976), it is very likely that the compounds of the present invention will show a highly potent antipsychotic action in man.

TABLE II

The ability to block apomorphine induced stereotypes and hyperactivity

| Compound | Structure | Block of apomorphine $ED_{50}$, μmol/kg i.p. | |
|---|---|---|---|
| | | stereotypes | hyperactivity |
| Sulpiride | | 203 | 50 |
| FLA 731 | 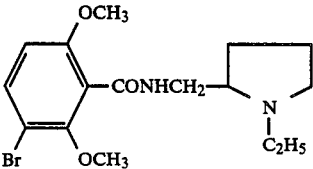 | 23 | 11 |
| FLA 731 (−) | | 5.6 | 0.83 |
| FLA 797 | 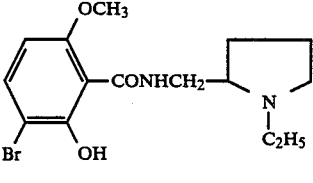 | 1.1 | 0.22 |
| FLA 797 (−) | | 0.38 | 0.035 |
| FLA 814 | 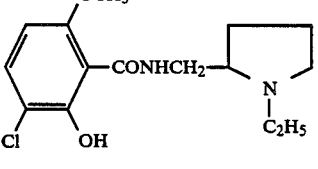 | — | — |
| FLA 814 (−) | | 1.1 | 0.14 |
| FLA 659 | 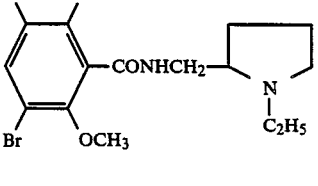 | — | — |
| FLA 659 (−) | | 2.3 | 0.40 |

TABLE II-continued
The ability to block apomorphine induced stereotypes and hyperactivity

| Compound | Structure | Block of apomorphine $ED_{50}$, μmol/kg i.p. stereotypes | hyperactivity |
|---|---|---|---|
| FLA 901 | 4-Br, 2-OH, 3-OC$_2$H$_5$ benzamide -CONHCH$_2$-(N-ethyl pyrrolidin-2-yl) | 3.4 | 1.1 |
| FLA 908 | 4-Br, 2-OH, 3-OCH$_3$ benzamide -CONHCH$_2$-(N-ethyl pyrrolidin-2-yl) | 10 | 1.1 |
| FLA 870 | 3,5-diCl, 2-OH, 6-OCH$_3$ wait — 3-Cl, 5-Cl, 6-OH, 2-OCH$_3$ benzamide -CONHCH$_2$-(N-ethyl pyrrolidin-2-yl) | | |
| FLA 870 (−) | | 2.4 | 0.11 |
| FLA 903 | 2-OCH$_3$, 6-OCCH$_3$(=O), 3-Br benzamide -CONHCH$_2$-(N-ethyl pyrrolidin-2-yl) | 0.53 | 0.28 |
| FLA 889 | 2-OCH$_3$, 6-OH, 3-Br benzamide -CONHCH$_2$-(N-propyl pyrrolidin-2-yl) | | |
| FLA 889 (−) | | 0.75 | 0.27 |

The compounds of the invention were also compared to sulpiride in the same test system after oral administration. The results are tabulated below.

TABLE III
The potency to block apomorphine following oral administration to the rat

| Compound acc. to Example no. | $ED_{50}$, μmol/kg p.o. Stereotypies | Hyperactivity |
|---|---|---|
| 797(−) | 22 | 3 |
| 814(−) | 25 | 4.4 |
| 901(−) | 34 | 3.0 |
| 659(−) | 12 | 3.2 |
| Sulpiride | >586 | >586 |

As can be seen sulpiride has lost all activity. This is in contrast to the tested compounds of the invention, which are still highly effective after oral administration to the rat.

BEST MODE OF CARRYING OUT THE INVENTION

Among the compounds of the present invention according to formula I the levo-rotatory enantiomers of N-ethyl-2-(5-chloro-2-hydroxy-6-methoxybenzamidomethyl)pyrrolidine, N-ethyl-2-(3,5-dibromo-2-hydroxy-6-methoxybenzamidomethyl)pyrrolidine, N-ethyl-2-(3,5-diethyl-2-hydroxy-6-methoxybenzamidomethyl)pyrrolidine, N-ethyl-2-(3-bromo-2-hydroxy-6-methoxybenzamidomethyl)pyrrolidine and their use for the treatment of psychosis represent the best mode known at present.

What is claimed is:
1. A compound of formula

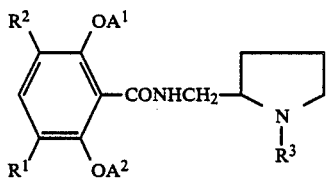

wherein $R^1$ and $R^2$ are the same or different and each represents a hydrogen atom, a halogen atom, a cyano group, a lower alkyl group which may be straight or branched and has from 1 to 5 carbon atoms or an acyl group having the formula alkyl—CO— wherein the alkyl moiety is straight or branched and has from 1 to 5 carbon atoms, $R^3$ is a lower alkyl group which may be straight or branched and has from 1 to 5 carbon atoms; and alkenyl group which may be straight or branched and has from 2 to 5 carbon atoms and has at least one double bond; or a benzyl group, wherein said benzyl group is optionally substituted with fluorine, chlorine, bromine, trifluoromethyl, lower alkyl which may be straight or branched and has from 1 to 5 carbon atoms or lower alkoxy having the formula alkyl-O wherein the alkyl moiety is straight or branched and has from 1 to 5 carbon atoms or any combination thereof, one of $A^1$ and $A^2$ is a lower alkyl group which may be straight or branched and has from 1 to 5 carbon atoms, and the other of $A^1$ and $A^2$ is a hydrogen atom; or a physiologically acceptable salt or optical isomer thereof.

2. A compound according to claim 1; (—)-N-ethyl-2-(3-bromo-2-hydroxy-6-methoxybenzamidomethyl)pyrrolidine.

3. A compound according to claim 1; (—)-N-ethyl-2-(3,5-dibromo-2-hydroxy-6-methoxybenzamidomethyl)-pyrrolidine.

4. A compound according to claim 1; (—)-N-ethyl-2-(5-chloro-2-hydroxy-6-methoxybenzamidomethyl)pyrrolidine.

5. A compound according to claim 1; (—)-N-ethyl-2(3,5-diethyl-2-hydroxy-6-methoxybenzamidomethyl)-pyrrolidine.

6. A compound according to claim 1; (—)-N-ethyl-2-(3,5-dichloro-6-hydroxy-2-methoxybenzamidomethyl)-pyrrolidine.

7. A compound of formula

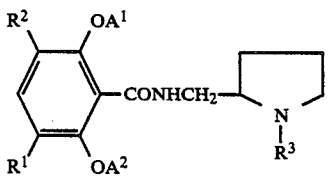

wherein $R^1$ and $R^2$ are the same or different and each represents a hydrogen atom, a halogen atom, a cyano group, a lower alkyl group which may be straight or branched and has from 1 to 5 carbon atoms or an acyl group having the formula alkyl—CO— wherein the alkyl moiety is straight or branched and has from 1 to 5 carbon atoms, $R^3$ is a lower alkyl group which may be straight or branched and has from 1 to 5 carbon atoms; an alkenyl group which may be straight or branched and has from 2 to 5 carbon atoms and has at least one double bond; or a benzyl group, wherein said benzyl group is optionally substituted with fluorine, chlorine, bromine, trifluoromethyl, lower alkyl which may be straight or branched and has from 1 to 5 carbon atoms or lower alkoxy having the formula alkyl-O wherein the alkyl moiety is straight or branched and has from 1 to 5 carbon atoms or any combination thereof, one of $A^1$ and $A^2$ is a lower alkyl group which may be straight or branched and has from 1 to 5 carbon atoms, and the other of $A^1$ and $A^2$ is an acyl group having the formula alkyl—CO— wherein the alkyl moiety is straight or branched and has from 1 to 5 carbon atoms, or an alkoxycarbonyl group having the formula alkyl—O—CO— wherein the alkyl moiety is straight or branched and has from 1 to 5 carbon atoms, or a dialkylcarbamyl group having the formula $(alkyl)_2$—N—CO— wherein the alkyl moiety is straight or branched and has from 1 to 5 carbon atoms; or a physiologically acceptable salt or optical isomer thereof.

8. A compound according to claims 1 or 7 wherein $R^3$ is a lower alkyl group other than ethyl; an alkenyl group; or a benzyl group optionally substituted with fluorine, chlorine, bromine, trifluoromethyl, lower alkyl or lower alkoxy.

9. A compound according to claim 8 in the form of an optical isomer thereof.

10. A compound according to claim 9 in the form of a physiologically acceptable salt thereof.

11. A pharmaceutical preparation comprising as active ingredient a compound according to claim 10 or a physiologically acceptable salt or optical isomer thereof in association with a pharmaceutically acceptable carrier.

12. A pharmaceutical preparation according to claim 11 in dosage unit form.

13. A pharmaceutical preparation according to claim 12 comprising the active ingredient in association with a pharmaceutically acceptable carrier.

14. A method for the treatment of emesis in man characterized by the administration to a host in need of such treatment of an amount effective to block the dopamine receptors of the brain of a compound according to claim 10.

15. A method for the treatment of psychosomatic diseases in man characterized by the administration to a host in need of such treatment of an amount effective to block the dopamine receptors of the brain of a compound according to claim 10.

16. A method for the treatment of psychiatric disorders in man characterized by the administration to a host in need of such treatment of an amount effective to block the dopamine receptors of the brain of a compound according to claim 10.

* * * * *